United States Patent [19]

Koeda et al.

[11] 4,156,728

[45] May 29, 1979

[54] 3-SUBSTITUTED-2(1H)PYRIDONE-6-CARBOXYLIC ACIDS

[75] Inventors: Takemi Koeda, Yokohama; Takashi Tsuruoka, Kawasaki; Hiroyasu Asaoka, Yokohama; Uichi Shibata, Tokyo; Shigeharu Inoue; Taro Niida, both of Yokohama, all of Japan

[73] Assignee: Meiji Seika Kaisha, Ltd., Japan

[21] Appl. No.: 865,213

[22] Filed: Dec. 28, 1977

Related U.S. Application Data

[63] Continuation-in-part of Ser. No. 700,340, Jun. 28, 1976, Pat. No. 4,083,850.

[30] Foreign Application Priority Data

Jun. 30, 1975 [JP] Japan .................................. 50-80102
Jun. 30, 1975 [JP] Japan .................................. 50-80103

[51] Int. Cl.$^2$ .................. A61K 31/44; A61K 213/79
[52] U.S. Cl. ..................................... 424/266; 546/296
[58] Field of Search ....................... 260/295 R, 295 L; 424/266; 546/296

[56] References Cited

U.S. PATENT DOCUMENTS 3,355,278 11/1967 Weil et al. ........................ 260/295 L

FOREIGN PATENT DOCUMENTS 1016676 7/1974 Japan .................................. 260/295 R

OTHER PUBLICATIONS

Kametani et al., Chemical Abstracts, vol. 74 (1971), 133311e.
Stetter et al., Chemical Abstracts, vol. 52 (1958), 91290.

Primary Examiner—Richard Raymond
Attorney, Agent, or Firm—McGlew and Tuttle

[57] ABSTRACT

Novel compounds useful as hypotensive agents are presented having the general formula I

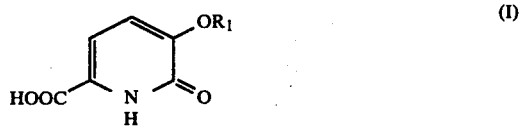

wherein $R_1$ represents a substituted or unsubstituted aralkyl group, that is an aralkyl group of the general formula

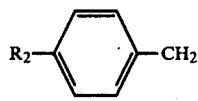

wherein $R_2$ represents hydrogen, a lower alkyl group or a halogen atom. Furthermore, new therapeutic compositions of matter are also described incorporating the above novel 3-substituted-2(1H)pyridone-6-carboxylic acids (I) as an active ingredient with carriers and showing uses as hypotensive agents. These new compounds of the formula I are prepared by reacting D-glucaro-δ-lactam or its salt with an aralkyl halide.

9 Claims, No Drawings

3-SUBSTITUTED-2(1H)PYRIDONE-6-CARBOXYLIC ACIDS

CROSS REFERENCE TO RELATED APPLICATION

This application is a continuation-in-part of copending application Ser. No. 700,340, filed June 28, 1976, now U.S. Pat. No. 4,083,850.

DESCRIPTION OF THE INVENTION

This invention relates to 3-substituted-2(1H)pyridone-6-carboxylic acids, and therapeutic compositions of matter formed from the same.

An object of the present invention is to provide 3-substituted-2(1H)pyridone-6-carboxylic acids of the general formula I

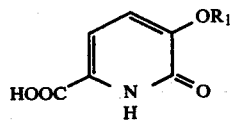

wherein $R_1$ stands for a substituted or unsubstituted aralkyl group, preferably an aralkyl group of the formula

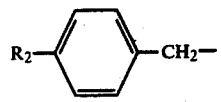

wherein $R_2$ stands for hydrogen, a lower alkyl group or a halogen atom, where "lower" means a group having from one to six carbon atoms.

Another object is to provide compositions useful in lowering blood pressure in mammals.

The compounds wherein $R_1$ is an aralkyl group of the formula

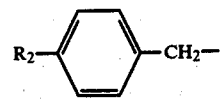

wherein $R_2$ has the same meaning as described above can be prepared by reacting 3-hydroxy-2(1H)pyridone-6-carboxylic acid of the formula II

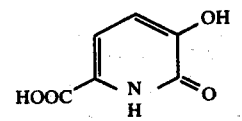

with an alkyl, alkenyl or aralkyl halide of the general formula III

 (III)

wherein $R_1$ stands for the same meaning as described just above and X stands for a halogen atom.

D-glucaro-δ-lactam, one of the starting materials for Method 1, is easily available, for example by oxidation of antibiotic Nojirimycin in accordance with the method which was also found by us. (See U.S. Pat. No. 3,956,337, column 3, lines 40–45).

When D-glucaro-δ-lactam in the form of free acid or its salt such as sodium or potassium salt is treated in pyridine with an acid anhydride in the cold or at room temperature (e.g. at temperatures of 0.25° C.), the corresponding tetraacyl derivative results as expected.

It has now been surprisingly found that when this reaction is carried out under heating a dehydration reaction takes place to form the corresponding 3-acyloxy-2(1H)pyridone-6-carboxylic acid.

3-Hydroxy-2(1H)pyridone-6-carboxylic acid, one of the starting materials is easily available for example by deacylation of a 3-acyloxy-2(1H)pyridone-6-carboxylic acid which can be prepared as described above.

In carrying out this preparation, 3-hydroxy-2(1H)pyridine-6-carboxylic acid of the formula II is reacted in a solvent and a base with an alkyl, alkenyl or aralkyl halide of the general formula III to cause selective substitution of the 3-hydroxyl group. Suitable examples of the solvent include water, organic solvents miscible with water and mixtures of them such as water/alcohol, water/dioxan, water/acetone or the like. Suitable examples of the base include inorganic bases such as sodium hydroxide, potassium hydroxide, sodium carbonate, potassium carbonate or sodium hydrogen carbonate, and organic bases such as triethylamine.

In this reaction little substitution at the >NH in the pyridone ring is found to take place, which is considered to be due to steric hindrance by the 6-carboxyl group.

This reaction proceeds also in an organic solvent such as alcohols, dioxan or acetone, although in this case a substitution reaction at the carboxyl group takes place simultaneously. It is of course possible to convert the thus formed esters into the desired compounds in an easy manner, for example by hydrolysis with an acid or alkali.

When an alkyl halide is used, the reaction temperature is preferably in the range of from 40° to 100° C. When an alkenyl or aralkyl halide is used, the reaction proceeds smoothly at a temperature of from room temperature to 70° C.

Some of the halides may cause more or less side-reaction products to form which, however, can be removed easily by any suitable work-up operation, such as solvent extraction, precipitation or crystallization.

The compounds according to the present invention all show a hypotensive effect and therefore are useful as pharmaceuticals.

With a view to exhibiting the hypotensive effect of the compounds of the invention, the following pharmacological test was conducted for some examples of the compounds:

To a group consisting of three to five 20–25 week old rats having spontaneous hypertension was administered, either intraperitoneally or orally, the compound to be tested suspended in a 1% gum arabic (acacia) solution). The change of blood pressure was measured in each case by the tail volume method to give the following results:

| Compound | Dose in mm/kg | Route of Administration | Blood pressure before administration in mm Hg | Blood pressure after administration in mm Hg | | | |
|---|---|---|---|---|---|---|---|
| | | | | After 1 hr. | After 2 hrs. | After 4 hrs. | After 6 hrs. |
| 3-(p-Ethylbenzyloxy)-2(1H)pyridone-6-carboxylic acid | 50 | intraperitoneal | 185 | — | 172 | 161 | 168 |

EXAMPLE 1: PREPARATION OF INTERMEDIATE 52 g of 3-acetoxy-2(1H)pyridone-6-carboxylic acid was suspended in 500 cc of distilled water and 20 g of sodium hydroxide added to the suspension. The mixture was warmed to 60° C. for 30 minutes. The resulting reaction mixture was adjusted to pH 2 with 5 N hydrochloric acid, whereupon crystals are immediately precipitated. After the reaction mixture was allowed to stand in the cold, the crystals were filtered off and dried in a dessicator to obtain 45 g of 3-hydroxy-2(1H)pyridine-6-carboxylic acid in the form of white needle crystals.

A sample recrystallized from hot water was analyzed to give the following results Melting point: 248°–249° C. Elemental Analysis: Found (%) C 41.48, H 3.89, N 8.15 Calcd. for $C_6H_5O_4N \cdot H_2O$(%) C 41.62, H 4.08, N 8.09.

EXAMPLE 2: PREPARATION OF UNSUBSTITUTED ARALKYL COMPOUND 1.5 g of 3-hydroxy-2(1H)pyridone-6-carboxylic acid was suspended in a mixture of 20 cc of water and 20 cc of methanol. To this suspension was added 1.2 g of sodium hydroxide, whereupon the carboxylic acid dissolved. Subsequently 4 cc of benzyl bromide was added and the mixture stirred at 60° C. for 12 hours. The reaction mixture was adjusted to pH 1.8 with 5 N hydrochloric acid and concentrated to approximately 8 cc, whereupon crystals precipitated. The crystals were recrystallized from chloroform/ethanol to obtain 1.8 g of 3-benzyloxy-2(1H)pyridone-6-carboxylic acid in the form of white needle-like crystals.

Melting point: 225°–226° Elemental Analysis: Found (%) C 63.20, H 4.65, N 5.57 Calcd. for $C_{13}H_{11}O_4N$(%) C 63.67, H 4.52, N 5.71.

EXAMPLE 3: PREPARATION OF HALOGEN-SUBSTITUTE ARALKYL COMPOUND 15 cc of water is added to 1.4 g of 3-hydroxy-2(1H)pyridone-6-carboxylic acid. Subsequently 2.3 g of sodium carbonate was added, whereupon the carboxylic acid dissolved. After 4 cc of p-chlorobenzyl chloride was added, the reaction was carried out by stirring the resulting mixture at 65° C., causing precipitation of crystals to take place. After a nine hour reaction, the reaction mixture was cooled and filtered to obtain 1.9 g of sodium 3-(-chlorobenzyloxy)-2(1H)pyridine-6-carboxylate in the form of white crystals.

0.3 g of the product was dissolved in 30 cc of water and the solution adjusted to pH 1.8 with 5 N hydrochloric acid and extracted with chloroform. The chloroform phase was directly concentrated to dryness. The residue was recrystallized from hot ethanol to obtain 0.2 g of 3-(p-chlorobenzyloxy)-2-(1H)-pyridone-6-carboxylic acid in the form of white needle crystals.

Melting point: Elemental Analysis: Found % C 56.12, H 3.63, N 4.98; Calcd. for $C_{13}H_{10}O_4N \cdot Cl$(%) C 55.83, H 3.60, N 5.01.

EXAMPLE 4: PREPARATION OF LOWER ALKYL SUBSTITUTED ARALKYL COMPOUND 50 cc of water was added to 1.5 g of 3-hydroxy-2(1H)pyridone-6-carboxylic acid. Subsequently 3g of sodium carbonate was added, whereupon the carboxylic acid dissolved. To the mixture was added dropwise, with stirring at 55° C. over a period of 2 hours, 20 cc of ethanol containing 4 cc of p-ethylbenzyl chloride. After the reaction was continued at the same temperature for an additional 2 hours, the reaction mixture was concentrated to remove the ethanol.

The reaction mixture (pH 8) was extracted with 10 cc of chloroform to remove impurities, adjusted to pH 1.8 with 5 N hydrochloric acid and extracted with 30 cc of chloroform. The chloroform extract was concentrated to approximately 30 cc. After addition of 8 cc of ethanol, the concentrate was allowed to stand in the cold, whereupon crystals precipitated. The crystals were filtered off to obtain 830 mg of 3-(p-ethylbenzyloxy)-2(1H)pyridone-6-carboxylic acid in the form of white particulate crystals.

Melting Point: 203°–204° C. Elemental Analysis: Found (%) C 65.80, H 5.50, N 4.99; Calcd. for $C_{15}H_{15}O_4N$(%) C 65.92, H 5.53, N 5.13.

EXAMPLE 5: PREPARATION OF LOWER ALKYL SUBSTITUTED ARALKYL COMPOUND 3 g. of 3-hydroxy-2(1H) 6-carboxylic acid and 5 g of sodium carbonate were dissolved in 80 cc of water. To this mixture was added dropwise, with stirring at 50° C. over a period of one hour, 20 cc of ethanol containing 7 cc of p-methylbenzyl chloride. After the reaction was continued at the same temperature for a further three hours, the reaction mixture was adjusted to pH 1.8 with 5 N hydrochloric acid and extracted with 50 cc of chloroform.

The chloroform extract was concentrated to approximately 4 cc, and upon addition of 30 cc of ethyl ether precipitation of crystals took place. The crystals were recrystallized from chloroform/ethanol to obtain 1.2 g of 3-(p-methylbenzyloxy)-2(1H)-pyridone-6-carboxylic acid in the form of white needle crystals.

Melting point: 201°–202° C. Elemental analysis: Found (%) C 65.13, H 5.22, N 5.38 Calcd. for $C_{14}H_{13}O_4N$ (%) C 64.36, H 5.05, N 5.4.

Further illustration of the invention is as follows:

One g of 3-hydroxy-2(1H)pyridone-6-carboxylic acid was suspended in a mixture of 15 cc pyridine and 5 cc propionic anhydride, followed by stirring at room temperature.

3-hydroxy-2(1H)pyridone-6-carboxylic acid dissolved slowly, precipitating reaction products.

After 24 hours, the reaction mixture was filtered off, to obtain 700 mg of 3-propionyl-2(1H)pyridone-6-carboxylic acid in the form of white powders.

What is claimed is:

1. A 3-substituted-2(1H)pyridine-6-carboxylic acid of the general formula

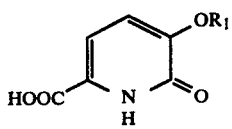

wherein $R_1$ is an aralkyl group of the formula

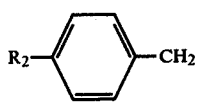

wherein $R_2$ is hydrogen, a lower alkyl group, or a halogen atom.

2. A compound according to claim 1, wherein $R_1$ is a functional group of the formula

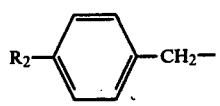

wherein $R_2$ is hydrogen, chlorine, methyl or ethyl.

3. A compound according to claim 1, wherein $R_1$ is the benzyl group.

4. A compound according to claim 1, wherein $R_1$ is the p-chlorobenzyl group.

5. A compound according to claim 1, wherein $R_1$ is the methylbenzyl group.

6. A compound according to claim 1, wherein $R_1$ is the ethylbenzyl group.

7. A therapeutic composition of matter for lowering the blood pressure which comprises (i) a therapeutically effective amount of a 3-substituted-2(1H)pyridone-6-carboxylic acid, and (ii) a pharmaceutically acceptable carrier, said 3-substituted-2(1H)pyridone-6-carboxylic acid (i) having the general formula

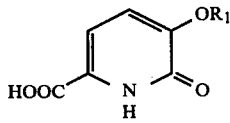

wherein $R_1$ is an aralkyl group of the formula

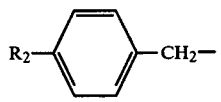

wherein $R_2$ is hydrogen, a lower alkyl group, or a halogen atom, and being suspended in said carrier (ii).

8. A therapeutic composition of matter according to claim 7, wherein said carrier is a gum arabic solution.

9. A therapeutic composition of matter according to claim 7, wherein $R_1$ is the p-ethylbenzyl group in (i).

* * * * *